United States Patent
Mao

(10) Patent No.: US 8,187,534 B2
(45) Date of Patent: May 29, 2012

(54) POROUS BARRIER MEDIA COMPRISING COLOR CHANGE INDICATORS

(75) Inventor: Guoqiang Mao, Smyrna, GA (US)

(73) Assignee: Porex Corporation, Fairburn, GA (US)

( * ) Notice: Subject to any disclaimer, the term of this patent is extended or adjusted under 35 U.S.C. 154(b) by 415 days.

(21) Appl. No.: 12/029,850

(22) Filed: Feb. 12, 2008

(65) Prior Publication Data

US 2008/0199363 A1    Aug. 21, 2008

Related U.S. Application Data

(60) Provisional application No. 60/900,817, filed on Feb. 12, 2007.

(51) Int. Cl.
*B01L 3/02* (2006.01)

(52) U.S. Cl. ...... 422/50; 422/68.1; 422/400; 210/510.1; 210/500.22; 210/500.34; 210/500.35; 210/500.38; 264/126; 264/127

(58) Field of Classification Search .............. 422/55, 422/56, 58, 82.05, 50, 68.1; 436/2, 116, 436/206; 210/510.1, 500.22, 500.34, 500.35, 210/500.38; 264/126, 127
See application file for complete search history.

(56) References Cited

U.S. PATENT DOCUMENTS

| | | | |
|---|---|---|---|
| 4,306,033 A | 12/1981 | Morita et al. | |
| 4,443,515 A | 4/1984 | Atlas | |
| 4,516,679 A | 5/1985 | Simpson et al. | |
| 4,724,114 A | 2/1988 | McFarland et al. | |
| 4,820,577 A | 4/1989 | Morman et al. | |
| 4,924,860 A | 5/1990 | Larsen et al. | |
| 4,999,164 A | 3/1991 | Puchinger et al. | |
| 5,156,811 A | 10/1992 | White | |
| 5,175,046 A | 12/1992 | Nguyen | |
| 5,259,956 A | 11/1993 | Mercer et al. | |
| 5,310,525 A | 5/1994 | Churchouse et al. | |
| 5,501,945 A | 3/1996 | Kanakkanatt | |
| 5,620,427 A | 4/1997 | Werschmidt et al. | |
| 5,750,585 A | 5/1998 | Park et al. | |
| 5,797,347 A | 8/1998 | Ochi | |
| 5,824,328 A | 10/1998 | Levy | |
| 5,836,929 A | 11/1998 | Bewick-Sonntag et al. | |
| 5,851,491 A | 12/1998 | Moulton | |
| 5,939,086 A | 8/1999 | Levy | |
| 5,998,032 A | 12/1999 | Hansen et al. | |
| 6,123,905 A | 9/2000 | Torti et al. | |
| 6,358,569 B1 | 3/2002 | Badyal et al. | |
| 6,638,610 B1 | 10/2003 | Yao | |

(Continued)

FOREIGN PATENT DOCUMENTS

DE    10157551    6/2003

(Continued)

OTHER PUBLICATIONS

Abstract of JP54111915 (Fuji Kagaku Shikogyo), Database WPI, Section Ch, Week 197941, Class A97, XP-002463794, AN-1979-74332B, Derwent Publications Ltd., London, GB, Sep. 1, 1979.
Abstract of JP57064537 (Showa Gum KK); Database WPI, Section Ch, Week 198221, Class A18, XP-002463797, AN-1982-42838E, Derwent Publications Ltd., London, GB, Apr. 19, 1982.

(Continued)

*Primary Examiner* — In Suk Bullock
*Assistant Examiner* — Sharon Pregler
(74) *Attorney, Agent, or Firm* — Kilpatrick Townsend & Stockton LLP

(57) ABSTRACT

The present invention provides porous barrier compositions comprising color change indicators and methods of making and using the same.

44 Claims, 4 Drawing Sheets

U.S. PATENT DOCUMENTS

| | | | |
|---|---|---|---|
| 7,743,642 B2 * | 6/2010 | Chiba et al. | 73/29.04 |
| 2003/0211799 A1 * | 11/2003 | Yao et al. | 442/361 |
| 2005/0109683 A1 * | 5/2005 | Joyce et al. | 210/94 |
| 2005/0192536 A1 | 9/2005 | Takagi et al. | |
| 2005/0273019 A1 | 12/2005 | Conway et al. | |
| 2005/0283093 A1 | 12/2005 | Conway et al. | |
| 2006/0018800 A1 | 1/2006 | Slowey et al. | |
| 2006/0177352 A1 | 8/2006 | Ziegmann et al. | |
| 2008/0197065 A1 | 8/2008 | Wingo et al. | |
| 2008/0199363 A1 | 8/2008 | Mao | |

FOREIGN PATENT DOCUMENTS

| | | |
|---|---|---|
| DE | 10157551 A1 | 6/2003 |
| EP | 0264704 B1 | 4/1988 |
| EP | 0301753 | 2/1989 |
| EP | 1688181 | 8/2006 |
| JP | 02117801 | 5/1990 |
| JP | 2004-331855 | 11/2004 |
| WO | WO-87/00439 | 1/1987 |
| WO | WO-96/06643 | 3/1996 |
| WO | WO-98/31465 | 7/1998 |
| WO | WO 02/36708 * | 5/2002 |
| WO | WO-02/36708 A2 | 5/2002 |
| WO | WO 2005053821 A1 * | 6/2005 |
| WO | WO-2006/097481 | 9/2006 |
| WO | WO 2006097481 A1 * | 9/2006 |
| WO | WO-2008/021539 A2 | 2/2008 |

OTHER PUBLICATIONS

Abstract of JP62225325 (Bando Chem Ind), Database WPI Week 198745, XP-002463793, AN-1987-317572, Derwent Publications Ltd., London, GB, Oct. 3, 1987.
Abstract of JP01171930 (Kinyosha KK), Database EPODOC, XP-002463792, European Patent Office, The Hague, NL, Jul. 6, 1989.
Abstract of JP03197097 (Pentel KK), Database WPI Week 199141, XP-002463795, AN-1991-298561, Derwent Publications Ltd., London, GB, Aug. 28, 1991.
Abstract of JP2000024428 (Mitsubishi Plastics Ind), Database WPI Week 200016, XP-002463796, AN-2000-175322, Derwent Publications Ltd., London, GB, Jan. 25, 2000.
Abstract of JP2004331855 (Toppan Printing Co), Database WPI Week 200401, XP-002485448, AN-2005-002909, Thomson Scientific, London, GB, Nov. 25, 2004.
PCT/US2007/018355 International Search Report and Written Opinion mailed Feb. 4, 2008.
PCT/US2008/001838 Invitation to Pay Fees and Partial Search Report mailed Jul. 7, 2008.
PCT/US2008/001838 International Search Report and Written Opinion mailed Aug. 26, 2008.
"EP07811431.1 Office Action dated Jun. 30, 2009".
"EP07811431.1 Response to Office Action dated Nov. 3, 2009".
"PCT/US2001/047056 International Search Report dated Jul. 24, 2002".
"PCT/US2008/001838 International Preliminary Report on Patentability dated Aug. 27, 2009".
"U.S. Appl. No. 11/894,066, Office Action dated Apr. 20, 2010".
"U.S. Appl. No. 11/894,066, Office Action dated Jul. 27, 2010".
EP 07811431.1, Office Action issued Oct. 28, 2010, 4 Pgs.
EP 08725464.5, Office Action issued Dec. 8, 2010, 3 Pgs.
Chinese Patent Application No. 200780039008.7, First Office Action mailed Nov. 26, 2010.
Chinese Patent Application No. 200780039008.7, Second Office Action mailed May 18, 2011.
European Patent Application No. 08725464.5, Response to First Office Action filed Apr. 15, 2011.
European Patent Application No. 08725464.5, Summons to Attend Oral Hearing mailed Sep. 23, 2011.
European Patent Application No. 07811431.1, Response to Second Office Action filed Mar. 3, 2011.
European Patent Application No. 07811431.1, Rule 71(3) EPC Communication regarding Intent to Grant Application mailed Apr. 29, 2011.
European Patent Application No. 08725464.5, Cancellation of Oral Proceedings mailed Jan. 23, 2012 (4 pages).
European Patent Application No. 08725464.5, Response filed Feb. 22, 2012 (49 pages).
Indian Patent Application No. 729KOLNP/2009, First Examination Report mailed Jan. 23, 2012 (6 pages).

* cited by examiner

POROUS BARRIER MEDIA COMPRISING COLOR CHANGE INDICATORS

PRIOR RELATED APPLICATION DATA

This application hereby claims priority to U.S. Provisional Patent Application Ser. No. 60/900,817, filed Feb. 12, 2007.

FIELD OF THE INVENTION

The present invention relates to porous barrier media and, in particular, to porous barrier media comprising color change indicators.

BACKGROUND OF THE INVENTION

Porous barrier media find application in a number of areas including liquid sampling and transfer apparatus, such as pipettes. Barrier media are often incorporated into liquid sampling and transfer apparatus to prevent contamination of the apparatus in situations where the liquid is overdrawn by human or mechanical error.

In addressing apparatus contamination, porous barrier media have incorporated absorbent materials which are operable to seal the pores of the media when exposed to liquid. The self-sealing nature of the barrier media comprising absorbent materials inhibits or prevents liquid from traveling through the media and contaminating downstream apparatus. In the sealed state, barrier media comprising absorbent materials additionally inhibit or prevent the flow of gasses thereby requiring replacement of the media for further liquid transfer or sampling.

In addition to absorbent materials, barrier media have been coated with metal salt color changing species, such as cobalt chloride. The coating of metal salt color changing species onto barrier media facilitates a determination of when the media has been contacted by fluid.

Several problems, however, exist with metal salt color changing species. Cobalt chloride, for example, is very sensitive to moisture and must be stored under extremely dry conditions in order to prevent color change before use. Moreover, the color change indication of cobalt chloride is slow leading to a delayed response upon contact of barrier media by a liquid. Many metal salts, including cobalt chloride, are toxic and, therefore, cannot be used in biological applications. Furthermore, metal salts coated onto porous barrier media can be displaced from the porous media and contaminate the liquid sample.

SUMMARY

In view of the foregoing problems, it would be desirable to provide porous barrier compositions comprising color change indicators that can provide a rapid response to contact by a liquid sample. Moreover, it would be desirable to provide porous barrier compositions comprising color change indicators that are stable to color change under ambient atmospheric or storage conditions. It would additionally be desirable to provide porous barrier compositions comprising color change indicators which resist contamination of liquid samples with toxic or biologically harmful species.

The present invention provides porous barrier compositions comprising color change indicators and methods of making and using the same. The present invention also provides apparatus comprising such porous barrier compositions.

In one embodiment, the present invention provides a self-sealing barrier composition comprising a sintered porous matrix, the sintered porous matrix comprising at least one plastic, at least one absorbent material, and at least one color change indicator. In some embodiments, the at least one absorbent material and the at least one color change indicator are homogeneously dispersed throughout the sintered porous matrix.

In some embodiments, at least one absorbent material comprises carboxymethylcellulose (CMC), cellulose gums, hydrolyzed acrylonitrile graft copolymer, neutralized starch-acrylic acid graft copolymer, acrylamide copolymer, modified crosslinked polyvinyl alcohol, neutralized self-crosslinking polyacrylic acid, crosslinked polyacrylate salts, or neutralized crosslinked isobutylene-maleic anhydride copolymers, or salts or mixtures thereof.

In some embodiments, at least one color change indicator comprises a dye, including, but not limited to, inorganic or organic dyes, such as food dyes, azo compounds, or azo dyes. In some embodiments, a color change indicator does not comprise inorganic salts, including transition metal salts. Additionally, in some embodiments, a color change indicator does not comprise a conjugate or complex that changes color upon the binding of an analyte. In some embodiments, compositions of the present invention do not comprise proteins or other biological molecules.

A color change indicator, according to embodiments of the present invention, is operable to at least partially change the color of the sintered porous matrix when contacted with an aqueous and/or organic liquid. In some embodiments, the color change indicator changes the sintered porous matrix from a first color to a second color when contacted with an aqueous and/or organic liquid. In other embodiments, the color change indicator changes the sintered porous matrix from colorless or white to colored. The color change of the sintered porous matrix, according to embodiments of the present invention, depends on the identity of the color change indicator selected. The change in color provides an indication to a user that the self-sealing barrier composition has come into contact with a liquid.

In another embodiment, the present invention provides a self-sealing barrier composition comprising a sintered porous matrix, the sintered porous matrix comprising at least one self-sealing layer comprising an absorbent material and at least one indicator layer comprising at least one color change indicator. In some embodiments, the indicator layer is adjacent to the self-sealing layer. In other embodiments, the indicator layer is spaced apart from the self-sealing layer. In one embodiment, the self-sealing layer further comprises a first plastic. In another embodiment, the indicator layer further comprises a second plastic. In some embodiments, the first plastic and second plastic are the same. In other embodiments, the first plastic and second plastics are different. In some embodiments, the indicator layer further comprises at least one surfactant.

The self-sealing layer, in some embodiments, further comprises a color change indicator. In some embodiments, the color change indicator of the self-sealing layer is the same as the color change indicator of the indicator layer. In other embodiments, the color change indicator of the self-sealing layer is different than the color change indicator of the indicator layer.

In some embodiments, a self-sealing barrier composition comprises a plurality of self-sealing layers and a plurality of indicator layers.

"Self-sealing," as used herein, refers to the ability of the absorbent material to substantially close or seal pores of the porous matrix or a layer of the porous matrix such that the passage of liquid and/or gas is inhibited or prevented. Not all the pores of the porous matrix or a layer of the porous matrix are required to be substantially closed or sealed in order for the a composition to be self-sealing.

In another embodiment, the present invention provides a self-sealing barrier composition comprising a sintered porous matrix, the sintered porous matrix comprising a self-sealing surface and an indicator surface in facing opposition to the self-sealing surface, the self-sealing surface comprising an absorbent material and the indicator surface comprising a color change indicator. In one embodiment, the self-sealing surface further comprises a first plastic. In another embodiment, the indicator surface further comprises a second plastic. In one embodiment, the first plastic and second plastic are the same. In other embodiments, the first plastic and second plastic are different. In some embodiments, the indicator surface further comprises at least one surfactant.

The self-sealing surface, in some embodiments, further comprises a color change indicator. In some embodiments, the color change indicator of the self-sealing surface is the same as the color change indicator of the indicator surface. In other embodiments, the color change indicator of the self-sealing surface is different than the color change indicator of the indicator surface.

In addition to self-sealing barrier compositions, the present invention provides hydrophobic barrier compositions. In one embodiment, a hydrophobic barrier composition comprises a sintered porous matrix, the sintered porous matrix comprising at least one plastic and at least one color change indicator wherein the barrier composition is substantially free of any absorbent or self-sealing material. In some embodiments of a hydrophobic barrier composition, the sintered porous matrix does not comprise any absorbent or self-sealing material. As a result, hydrophobic barrier compositions, according to embodiments of the present invention, are not self-sealing. In one embodiment, at least one color change indicator comprises a dye, including, but not limited to, organic dyes, such as food dyes. Color change indicators, according to embodiments of the present invention, are operable to at least partially change the color of the sintered porous matrix when contacted with an aqueous and/or non-aqueous liquid. The change in color provides an indication to a user that the barrier material has come into contact with a liquid. In some embodiments, the at least one color change indicator is homogeneously dispersed throughout the sintered porous matrix.

In some embodiments, hydrophobic barrier compositions comprise a water intrusion pressure of greater than about 0.5 psi.

In another embodiment, the present invention provides a hydrophobic barrier composition comprising at least one plastic layer comprising at least a first plastic and an indicator layer comprising at least one color change indicator. In some embodiments, the at least one indicator layer is adjacent to the at least one plastic layer. In other embodiments, the at least one indicator layer is spaced apart from the at least one plastic layer. In one embodiment, the at least one indicator layer further comprises a second plastic. In some embodiments, the second plastic is the same as the first plastic. In other embodiments, the second plastic is different than the first plastic. In some embodiments, the indicator layer further comprises at least one surfactant.

The plastic layer, in some embodiments, further comprises a color change indicator. In some embodiments, the color change indicator of the plastic layer is the same as the color change indicator of the indicator layer. In other embodiments, the color change indicator of the plastic layer is different than the color change indicator of the indicator layer.

In a further embodiment, the present invention provides a hydrophobic barrier composition comprising a sintered porous matrix, the sintered porous matrix comprising a first surface and a second surface in facing opposition to the first surface, the first surface comprising at least one plastic and the second surface comprising at least one color change indicator. In some embodiments, the second surface comprises at least one surfactant. In another embodiment, the first surface further comprises a color change indicator. In some embodiments, the color change indicator of the first surface is the same as the color change indicator of the second surface. In other embodiments, the color change indicator of the first surface is different than the color change indicator of the second surface.

In another embodiment, the present invention provides a hydrophilic composition comprising a sintered porous matrix, the sintered porous matrix comprising at least one plastic, at least one color change indicator, and at least one surfactant.

In some embodiments of a sintered porous matrix of barrier compositions of the present invention, the color change indicator is locked within the sintered porous matrix. In being locked within the sintered porous matrix, the color change indicator, in some embodiments, is not a coating. Moreover, in some embodiments, the color change indicator at least partially resides in the pores of a sintered porous matrix. In a further embodiment, the color change indicator is locked in the sintered porous matrix and additionally resides in the pores of the sintered porous matrix.

In another aspect, the present invention provides methods of producing barrier compositions. In one embodiment, a method of producing a self-sealing barrier composition comprises providing particles of at least one plastic, providing particles of at least one absorbent material, providing particles of at least one color change indicator, and sintering the particles of the at least one plastic, the at least one absorbent material, and the at least one color change indicator.

In another embodiment, a method of producing a self-sealing barrier composition comprises disposing particles of at least one absorbent material in a first part of a mold, disposing particles of at least one color change indicator in a second part of the mold adjacent to the first part of the mold, and sintering the particles of the at least one absorbent material and color change indicator. In some embodiments particles of a first plastic are mixed with the particles of the at least one absorbent material prior to sintering. In some embodiments, particles of a second plastic are mixed with particles of the at least one color change indicator prior to sintering. In one embodiment, the first plastic and the second plastic are the same. In another embodiment, the first plastic and the second plastic are different.

In some embodiments, particles of at least one surfactant are mixed with particles of the at least one color change indicator prior to sintering. In other embodiments, particles of a second plastic are at least partially coated with at least one surfactant prior to sintering. In such embodiments, the surfactant can be applied to the second plastic particles as a liquid. In some embodiments, particles of a second color change indicator are mixed with particles of the at least one absorbent material prior to sintering. In some embodiments, particles of the at least one color change indicator and particles of the second color change indicator are the same. In another embodiment, particles of the at least one color change indicator and particles of the second color change indicator are different.

In another embodiment, a method for producing a hydrophobic barrier composition comprises providing particles of at least one plastic, providing particles of at least one color change indicator, and sintering the particles of the at least one plastic and the at least one color change indicator.

In a further embodiment, a method for producing a hydrophobic barrier composition comprises disposing particles of a first plastic in a first part of a mold, disposing particles of at least one color change indicator in a second part of a mold adjacent to the first part of the mold, and sintering the particles of the first plastic and the at least one color change indicator. In some embodiments, particles of a second plastic are mixed with the particles of the at least one color change indicator prior to sintering. In one embodiment, the first plastic and second plastic are the same. In another embodiment, the first plastic and second plastic are different.

In some embodiments, particles of at least one surfactant are mixed with the particles of the at least one color change indicator prior to sintering. In other embodiments, particles of a second plastic are at least partially coated with at least one surfactant prior to sintering. In such embodiments, the surfactant can be applied to the second plastic particles as a liquid.

In another aspect, the present invention provides methods for producing hydrophilic compositions. In one embodiment, a method for producing a hydrophilic composition comprises providing particles of at least one plastic, providing particles of at least one color change indicator, providing particles of at least one surfactant, and sintering the particles of the at least one plastic, at least one color change indicator, and at least one surfactant. In another embodiment, a method for producing a hydrophilic composition comprises providing particles of at least one plastic, at least partially coating the particles of the at least one plastic with at least one surfactant, providing particles of at least one color change indicator, and sintering the particles of the at least one plastic and particles of the at least one color change indicator. In some embodiments, particles of color change indicators are at least partially coated with at least one surfactant prior to sintering.

In another aspect, the present invention provides apparatus comprising barrier compositions of the present invention. In one embodiment, an apparatus comprises a pipette tip, the pipette tip comprising a hollow tube having first and second open ends, a center member disposed between the first and second ends, the center member comprising a barrier composition according to any of the embodiments provided herein. The pipette tip can have any desired sample collection volume. In some embodiments, the pipette tip has a sample collection volume of about 10 μl or about 20 μl. In other embodiments, the pipette tip has a sample collection volume of about 50 μl or about 100 μl. In another embodiment, the pipette tip has a sample collection volume of about 200 μl, about 250 μl, about 500 μl, or about 1 ml. In a further embodiment, the pipette tip has a sample collection volume less than about 10 μl or greater than about 1 ml or about 5 ml. In some embodiments, the pipette tip has a sample collection volume of about 1 μl or about 5 μl.

In another embodiment, barrier compositions of the present invention find application as flow control devices in various apparatus such as aspirators. In one embodiment, an aspirator comprises a receptacle, a lid, and a barrier composition of the present invention disposed in the receptacle. The lid further comprises an inlet and an outlet wherein outlet is operable to be connected to a suction or vacuum line. In some embodiments, a self-sealing barrier composition, for example, covers the outlet such that when sufficient liquid has been collected in the receptacle, contact of the liquid to the barrier composition results in self-sealing of the composition. Sealing of the barrier composition prevents additional aspiration.

In another embodiment, barrier compositions of the present invention find application in needle apparatus such as an indwelling needle as described in U.S. patent application Ser. No. 11/065,579; a flashback blood collection needle as described in U.S. patent application Ser. No. 11/141,588; a blood collection set as described in U.S. patent application Ser. No. 11/141,446; and a luer cap associated with an intravenous (IV) set. In these applications, barrier compositions of the present invention are incorporated as vents, allowing the passage of air and other gases while blocking the passage of liquids such as blood.

In a further embodiment, barrier compositions of the present invention find application in analytical devices to indicate that sufficient liquid sample has been collected. In some embodiments, an analytical device comprises a liquid sample collection chamber comprising a sample inlet and a barrier composition disposed within the sample collection chamber. The barrier composition, in some embodiments, can be disposed at various levels in the collection chamber depending on the desired volume of sample to be collected. When sufficient sample has been collected, liquid contacts the barrier composition rendering a color change in the medium. The color change in the barrier composition can indicate to a user of the analytical device that sufficient sample has been collected. In some embodiments, the liquid sample chamber further comprises an outlet.

These and other embodiments of the present invention are described in greater detail in the detailed description which follows. These and other features and advantages of the present invention will become apparent after review of the following detailed description of the disclosed embodiments.

DETAILED DESCRIPTION

Figure 1:
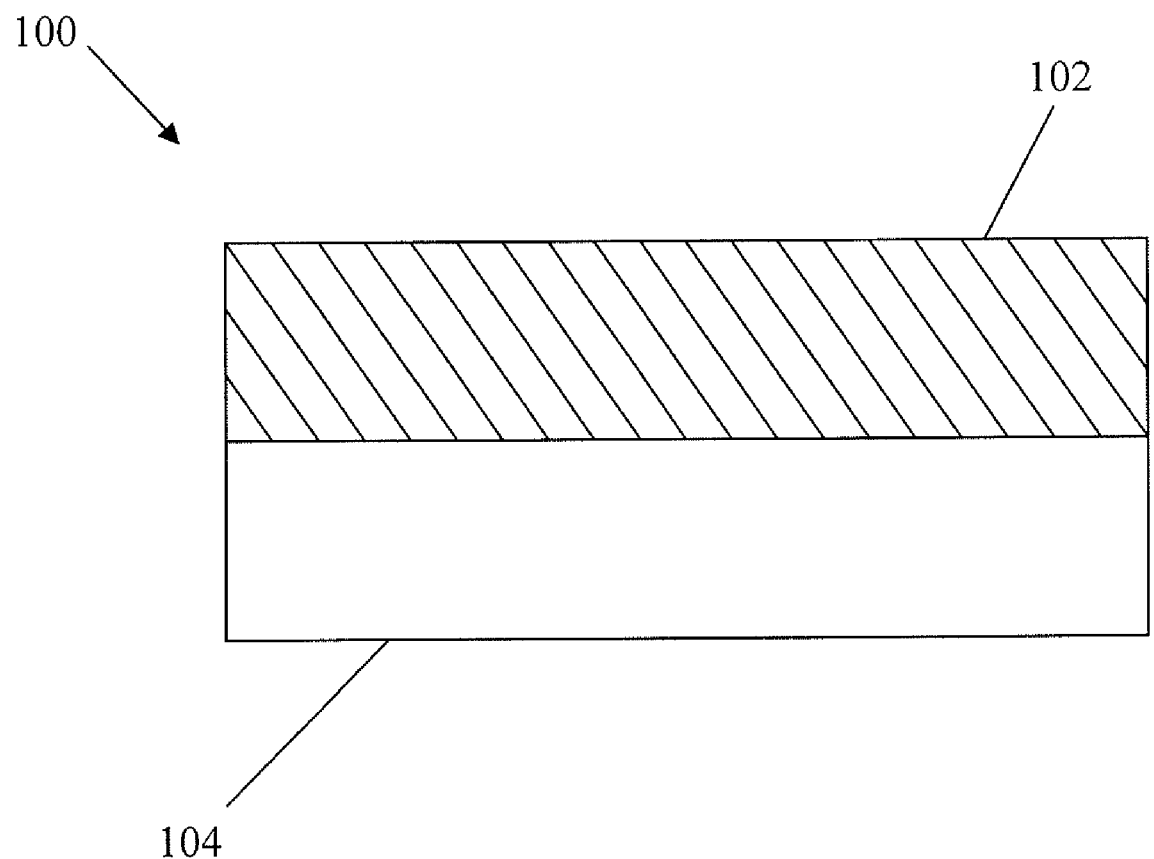
FIG. 1 illustrates a self-sealing barrier composition according to an embodiment of the present invention.

The present invention provides porous barrier compositions comprising color change indicators and methods of making and using the same. The present invention also provides apparatus comprising such porous barrier compositions.

Self-Sealing Barrier Compositions Comprising Color Change Indicators

In one embodiment, the present invention provides a self-sealing barrier composition comprising a sintered porous matrix, the sintered porous matrix comprising at least one plastic, at least one absorbent material, and at least one color change indicator.

Turning now to components that can be included in self-sealing barrier compositions of the present invention, self-sealing barrier compositions of the present invention comprise at least one plastic. In some embodiments, sintered porous matrices of self-sealing barrier compositions of the present invention comprise a plurality of plastics. Plastics, as used herein, include flexible plastics and rigid plastics. Flexible plastics, in some embodiments, comprise polymers possessing moduli ranging from about 15,000 N/cm$^2$ to about 350,000 N/cm$^2$ and/or tensile strengths ranging from about 1500 N/cm$^2$ to about 7000 N/cm$^2$. Rigid plastics, according to some embodiments, comprise polymers possessing moduli ranging from about 70,000 N/cm$^2$ to about 350,000 N/cm$^2$ and have tensile strengths ranging from about 3000 N/cm$^2$ to about 8500 N/cm$^2$.

Plastics suitable for use in sintered porous matrices of self-sealing barrier compositions, in some embodiments, comprise polyolefins, polyamides, polyesters, polyurethanes, polyacrylonitriles, polycarbonates, polyvinylchloride, polymethylmethacrylate, polyvinylidene fluoride, polytetrafluoroethylene, polyethersulfones, polystyrenes, polyether imides, polyetheretherketones, polysulfones, or combinations or copolymers thereof.

In some embodiments, a polyolefin comprises polyethylene, polypropylene, or copolymers thereof. Polyethylene, in one embodiment, comprises high density polyethylene (HDPE). HDPE, as used herein, refers to polyethylene having a density ranging from about 0.92 g/cm$^3$ to about 0.97 g/cm$^3$. In some embodiments, HDPE has a degree of crystallinity (% from density) ranging from about 50 to about 90. In another embodiment, polyethylene comprises ultrahigh molecular weight polyethylene (UHMWPE). UHMWPE, as used herein, refers to polyethylene having a molecular weight greater than 1,000,000.

In addition to at least one plastic, self-sealing barrier compositions comprise at least one absorbent material. In some embodiments, an absorbent material comprises carboxymethylcellulose (CMC), cellulose gums, hydrolyzed acrylonitrile graft copolymer, neutralized starch-acrylic acid graft copolymer, acrylamide copolymer, modified crosslinked polyvinyl alcohol, neutralized self-crosslinking polyacrylic acid, crosslinked polyacrylate salts, or neutralized crosslinked isobutylene-maleic anhydride copolymers, or salts or mixtures thereof. In other embodiments, absorbent materials comprise sodium polyacrylic acid and salts of poly (2-propenamide-co-2-propenoic acid).

In some embodiments, absorbent materials comprise those described by U.S. Pat. Nos. 5,998,032; 5,939,086; 5,836,929; 5,824,328; 5,797,347; 5,750,585; 5,175,046; 4,820,577; 4,724,114; and 4,443,515. Examples of commercially available absorbent materials include AP80HS from Stockhausen of Tuscaloosa, Ala., HYSORB® P7200 from BASF of Florham Park, N.J., and CMC under the product designation C5013 and C5678 from Sigma-Aldrich of St. Louis, Mo.

Absorbent materials, in some embodiments, can absorb greater than about 1, 50, 100, 200, 500, or 1000 percent of their weight in water while maintaining structural integrity.

Self-sealing barrier compositions of the present invention additionally comprise at least one color change indicator. A color change indicator, according to embodiments of the present invention, is operable to at least partially change the color of the sintered porous matrix when contacted with an aqueous and/or organic liquid. In some embodiments, the color change indicator changes the sintered porous matrix from a first color to a second color when contacted with an aqueous and/or organic liquid. In other embodiments, the color change indicator changes the sintered porous matrix from colorless or white to colored. In a further embodiment, the color change indicator changes the sintered porous matrix from a first shade of a color to a different shade of the same color. The color change of the sintered porous matrix, according to embodiments of the present invention, depends on the identity of the color change indicator selected.

In some embodiments, a color change indicator comprises an inorganic or organic dye, including food grade dyes, azo compounds, or azo dyes. In some embodiments, color change indicators do not comprise inorganic salts, including transition metal salts. Additionally, in some embodiments, a color change indicator does not comprise a conjugate or complex that changes color upon the binding of an analyte. In some embodiments, self-sealing barrier compositions of the present invention do not comprise proteins or other biological molecules.

Color change indicators comprising food grade dyes, according to embodiments of the present invention, are operable to be used with biological samples due to the non-toxic nature of the food dyes.

In some embodiments, a color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or combinations thereof.

Color change indicators, according to some embodiments, demonstrate a pH dependency on the color produced. As a result, color change indicators, in some embodiments, indicate not only liquid contact with the barrier composition but the relative pH of the contacting liquid as well. Color change indicators demonstrating a pH dependency, in some embodiments, comprise methyl violet, eosin yellow, malachite green, thymol blue, methyl yellow, bromophenol blue, congo red, methyl orange, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or combinations thereof.

A sintered porous matrix of a self-sealing barrier composition, according to some embodiments, comprises at least one plastic in an amount ranging from about 40 weight percent to about 95 weight percent of the matrix. In other embodiments, a sintered porous matrix comprises at least one plastic in an amount ranging from about 50 weight percent to about 90 weight percent of the matrix. In a further embodiment, a sintered porous matrix comprises at least one plastic in an amount ranging from about 60 weight percent to about 80 weight percent of the matrix.

A sintered porous matrix of a self-sealing barrier composition, in some embodiments, comprises at least one absorbent material in an amount ranging from about 1 weight percent to about 40 weight percent of the matrix. In other embodiments, a sintered porous matrix comprises an absorbent material in an amount ranging from about 5 weight percent to about 30 weight percent of the matrix. In a further embodiment, a sintered porous matrix comprises an absorbent material in an amount ranging from about 10 weight percent to about 20 weight percent of the matrix.

In addition to the at least one plastic and the at least one absorbent material, a sintered porous matrix of a self sealing barrier composition, in some embodiments, comprises at least one color change indicator in an amount ranging from about 0.001 weight percent to about 2 weight percent of the matrix. In other embodiments, a sintered porous matrix comprises at least one color change indicator in an amount ranging from about 0.01 weight percent to about 1 weight percent of the matrix. In a further embodiment, a sintered porous matrix comprises at least one color change indicator in an amount ranging from about 0.05 weight percent to about 0.5 weight percent of the matrix.

A sintered porous matrix of a self-sealing barrier composition comprising at least one plastic, at least one absorbent material, and at least one color change indicator, has a porosity ranging from about 10% to about 90%. In another embodiment, a sintered porous matrix has a porosity ranging from about 20% to about 80% or from about 30% to about 70%. In a further embodiment, a sintered porous matrix has a porosity ranging from about 40% to about 60%.

A sintered porous matrix of a self-sealing barrier composition comprising at least one plastic, at least one absorbent material, and at least one color change indicator, has an average pore size ranging from about 1 µm to about 200 µm. In other embodiments, a sintered porous matrix has an average pore size ranging from about 2 µm to about 150 µm, from about 5 µm to 100 µm, or from about 10 µm to about 50 µm. In another embodiment, a sintered porous matrix has a an average pore size less than about 1 µm. In one embodiment, a sintered porous matrix has an average pore size ranging from about 0.1 µm to about 1 µm. In a further embodiment, a sintered porous matrix has an average pore size greater than 200 µm. In one embodiment, a sintered porous matrix has an average pore size ranging from 200 µm to about 500 µm or from about 500 µm to about 1 mm.

In another embodiment, the present invention provides a self-sealing barrier composition comprising a sintered porous matrix, the sintered porous matrix comprising at least one self-sealing layer comprising at least one absorbent material and at least one indicator layer comprising at least one color change indicator. Absorbent materials suitable for use in the self-sealing layer of the present invention comprise any of the absorbent materials provided herein. Moreover, color change indicators suitable for use in the indicator layer comprise any of the color change indicators described herein.

In some embodiments, the self-sealing layer further comprises a first plastic. In some embodiments, the indicator layer further comprises a second plastic. In one embodiment, the first plastic and the second plastic are the same. In another embodiment, the first plastic and second plastic are different. Plastics suitable for use in embodiments of a barrier composition comprising at least one self-sealing layer and at least one indicator layer comprise any of the plastics described herein.

The indicator layer, in some embodiments, is adjacent to the self-sealing layer. In other embodiments, the indicator layer is spaced apart from the self-sealing layer. An indicator layer discrete from the self-sealing layer, in some embodiments, is operable to determine whether the self-sealing layer has completely sealed when contacted with an aqueous and/or organic liquid. In cases where the self-sealing layer does not sufficiently seal, an adjacent or spaced apart indicator layer can detect the presence of liquid that has breached the self-sealing layer which could potentially contaminate a downstream device, such as the suction apparatus of a pipette. In some embodiments wherein the indicator layer is spaced apart from the self-sealing layer, the self-sealing layer may further comprise a color change indicator operable to detect that a liquid has contacted the self-sealing layer.

In some embodiments, the self-sealing layer also comprises a color change indicator. In some embodiments, the color change indicator of the self-sealing layer is the same as the color change indicator of the indicator layer. In other embodiments, the color change indicator of the self-sealing layer is different than the color change indicator of the indicator layer. A self-sealing layer comprising a color change indicator can detect whether the self-sealing layer has been contacted by an aqueous and/or organic liquid.

In another embodiment, the indicator layer further comprises at least one surfactant. Surfactants, in some embodiments, comprise anionic surfactants, cationic surfactants, nonionic surfactants, amphoteric surfactants or mixtures thereof. In some embodiments, anionic surfactants comprise alkyl sulfates, alkylbenzenesulfonates, ether sulfates, α-olefin sulfonates, ester sulfonates, phosphate esters, acyl taurates, soaps, ether carboxylates, or mixtures thereof. Cationic surfactants, in some embodiments, comprise alkyl quaternary ammonium salts, bezylalkyldimethylammonium salts, amidoamine quaternaries, quaternary imidazolium compounds, ester quaternary compounds, or mixtures thereof. In some embodiments, nonionic surfactants comprise ethoxylated alcohols, ethoxylated alkylphenols, polyethylene glycol esters, fatty acid alkanolamides, ethoxylated alkanolamides, ethoxylated amines, esters of polyhydroxy compounds, ethoxylated esters, ethylene oxide/propylene oxide copolymers, amine oxides, or mixtures thereof. Amphoteric surfactants, in some embodiments, comprise alkylamino acids, alkylbetaines, alkylaminobetains, imidazoline-derived surfactants, sulfur containing amphoterics, lecithin, or mixtures thereof. In some embodiments, surfactants suitable for use in embodiments of the present invention comprise Geropon®, Rhodacal®, and Rhodafac® commercially available from Rhodia or Paris France, Pluronic® commercially available from BASF of Florham Park, N.J., and Zonyl® commercially available from DuPont of Wilmington, Del.

Indicator layers comprising at least one surfactant, in some embodiments, demonstrate advantageous wicking properties allowing a rapid response to an aqueous and/or organic liquid contacting the indicator layer.

In some embodiments, self-sealing layers can demonstrate any construction described herein for sintered porous matrices of self-sealing barrier compositions. Self-sealing layers, according to some embodiments, for example, can demonstrate pore sizes and/or porosities consistent with any the sintered porous matrices provided herein.

In some embodiments, indicator layers can demonstrate any construction described herein for sintered porous matrices of self-sealing barrier compositions. Indicator layers, according to some embodiments, for example, can demonstrate pore sizes and/or porosities consistent with any the sintered porous matrices provided herein.

In some embodiments, a self-sealing layer is constructed independently from an indicator layer. In such embodiments, the self-sealing layer and the indicator layer can display similar pore sizes and/or porosities or different pore sizes and/or porosities.

In some embodiments, at least one self-sealing layer comprises a plurality of self-sealing layers. At least one indicator layer, in some embodiments, comprises a plurality of indicator layers.

FIG. 1 illustrates a self-sealing barrier composition comprising a sintered porous matrix comprising at least one self-sealing layer and at least one indicator layer. The self-sealing barrier composition (100) illustrated in FIG. 1 comprises a indicator layer (102) adjacent to the self-sealing layer (104). Liquid breaching the self-sealing layer can contact the indicator layer thereby alerting a user of the barrier composition that the self-sealing layer has insufficiently sealed or has another problem allowing the passage of liquid.

In another embodiment, the present invention provides a self-sealing barrier composition comprising a sintered porous matrix, the sintered porous matrix comprising a self-sealing surface and an indicator surface in facing opposition to the self-sealing surface. The self-sealing surface of the barrier composition comprises at least one absorbent material, and the indicator surface comprises at least one color change indicator. Absorbent materials and color change indicators suitable for use in barrier compositions comprising a self-sealing surface and an indicator surface in facing opposition to the self-sealing surface comprise any of the same described herein.

An indicator surface disposed opposite of a self-sealing surface, in some embodiments, is operable to determine if the self-sealing surface has completely sealed when contacted with an aqueous and/or organic liquid. In cases where the self-sealing surface does not sufficiently seal, the opposing indicator surface can detect the presence of liquid that has breached the self-sealing surface which could potentially contaminate a downstream device In some embodiments, the self-sealing surface also comprises a color change indicator. In some embodiments, the color change indicator of the self-sealing surface is the same as the color change indicator of the indicator surface. In other embodiments, the color change indicator of the self-sealing surface is different than the color change indicator of the indicator surface. A self-sealing surface comprising a color change indicator can detect whether the self-sealing surface has been contacted by an aqueous and/or organic liquid.

In another embodiment, the indicator surface further comprises at least one surfactant. Surfactants suitable for indicator surfaces, according to embodiments of the present invention, comprise any of the surfactants provided herein. Indicator surfaces comprising at least one surfactant, in some embodiments, demonstrate advantageous wicking properties allowing a rapid response to an aqueous and/or organic liquid contacting the indicator surface.

Figure 2:
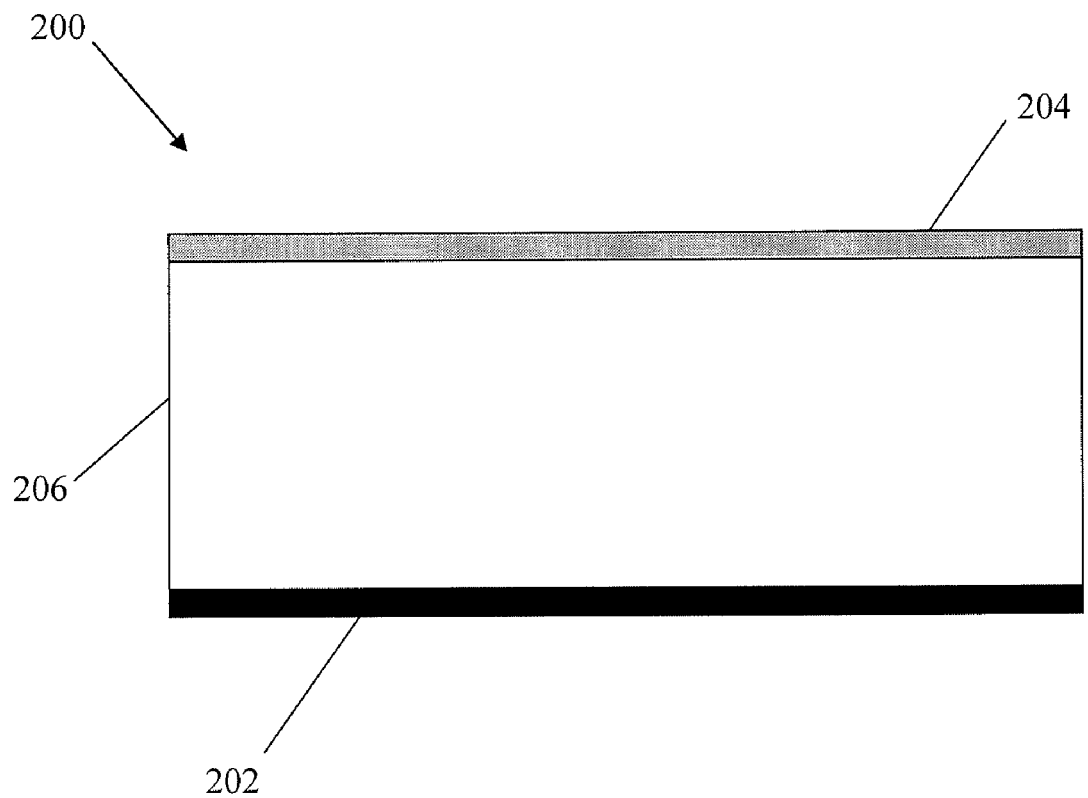
FIG. 2 illustrates a self-sealing barrier composition according to an embodiment of the present invention.

FIG. 2 illustrates a self-sealing barrier composition comprising a sintered porous matrix, the sintered porous matrix comprising at least one plastic, a self-sealing surface, and an indicator surface in facing opposition to the self-sealing surface. The barrier composition (200) of FIG. 2 comprises a self-sealing surface (202) and an indicator surface (204) in facing opposition to the self-sealing surface (202). A sintered porous plastic (206) is disposed between the self-sealing surface (202) and the indicator surface (204).

Self-sealing barrier compositions of the present invention, in some embodiments, exhibit a number of desirable properties including rapid response times, substantially no contamination of liquid samples, biocompatibility, and the ability to withstand high back pressures. In some embodiments, self-sealing barrier compositions can tolerate back pressures of greater than about 1, 2, or 5 pounds per square inch (psi). In some embodiments, self-sealing barrier compositions can tolerate back pressures up to about 20 psi. Moreover, air flow rate through self-sealing barrier compositions of the present invention, in some embodiments, is greater than about 16, 18, or 20 ml/minute. Self-sealing barrier compositions of the present invention, in some embodiments, are also stable when exposed to ambient environmental conditions. Self-sealing barrier compositions, in some embodiments, do not substantially respond to atmospheric moisture. In some embodiments, self-sealing barrier compositions of the present invention produce no color change in response to atmospheric moisture. As a result, self-sealing barrier compositions of the present invention can have a prolonged shelf life and require no special packaging or storage conditions.

Moreover, in providing a sintered porous matrix comprising an absorbent material, self-sealing barrier compositions of the present invention, in some embodiments, have substantially no absorbent particles disposed in the pores of the matrix. The absorbent material forms part of the sintered matrix. In some embodiments, a self-sealing barrier composition comprises no absorbent particles disposed in the pores of the matrix.

Hydrophobic Barrier Compositions Comprising Color Change Indicators

In addition to self-sealing barrier compositions, the present invention provides hydrophobic barrier compositions. In one embodiment, a hydrophobic barrier composition comprises a sintered porous matrix, the sintered porous matrix comprising at least one plastic and at least one color change indicator wherein the barrier material is substantially free of any absorbent or self-sealing material. In some embodiments, the sintered porous matrix of a barrier composition does not comprise any absorbent or self-sealing material. As a result, hydrophobic barrier compositions of the present invention are not self-sealing.

Turning now to components that can be included in hydrophobic barrier compositions of the present invention, hydrophobic barrier compositions of the present invention comprise at least one plastic. In some embodiments, sintered porous matrices of hydrophobic barrier compositions of the present invention comprise a plurality of plastics.

Plastics suitable for use in sintered porous matrices of hydrophobic barrier compositions, in some embodiments, comprise polyolefins, polyamides, polyesters, rigid polyurethanes, polyacrylonitriles, polycarbonates, polyvinylchloride, polymethylmethacrylate, polyvinylidene fluoride, polytetrafluoroethylene, polyethersulfones, polystyrenes, polyether imides, polyetheretherketones, polysulfones, or combinations or copolymers thereof.

In some embodiments, a polyolefin comprises polyethylene, polypropylene, and/or copolymers thereof. Polyethylene, in one embodiment, comprises HDPE. HDPE, as used herein, refers to polyethylene having a density ranging from about 0.92 g/cm$^3$ to about 0.97 g/cm$^3$. In some embodiments, HDPE has a degree of crystallinity (% from density) ranging from about 50 to about 90. In another embodiment, polyethylene comprises UHMWPE. UHMWPE, as used herein, refers to polyethylene having a molecular weight greater than 1,000,000.

In addition to at least one plastic, hydrophobic barrier compositions of the present invention comprise at least one color change indicator. A color change indicator, according to embodiments of the present invention, is operable to at least partially change the color of the sintered porous matrix when contacted with an aqueous and/or organic liquid. In some embodiments, the color change indicator changes the sintered porous matrix from a first color to a second color when contacted with an aqueous and/or organic liquid. In other embodiments, the color change indicator changes the sintered porous matrix from colorless or white to colored. In a further embodiment, the color change indicator changes the sintered porous matrix from a first shade of a color to a different shade of the same color. The color change of the sintered porous matrix, according to embodiments of the present invention, depends on the identity of the color change indicator selected.

In some embodiments, a color change indicator comprises an inorganic or organic dye, including food grade dyes, azo compounds, or azo dyes. In some embodiments, a color change indicator does not comprise inorganic salts, including transition metal salts. Additionally, in some embodiments, a color change indicator does not comprise a conjugate or complex that changes color upon the binding of an analyte. In some embodiments, hydrophobic barrier compositions of the present invention do not comprise proteins or other biological molecules.

Color change indicators comprising food grade dyes, according to embodiments of the present invention, are operable to be used with biological samples due to the non-toxic nature of the food dyes.

In some embodiments, a color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or combinations thereof.

Color change indicators, according to some embodiments, demonstrate a pH dependency on the color produced. As a result, color change indicators, in some embodiments, indicate not only liquid contact with the barrier composition but the relative pH of the contacting liquid as well. Color change indicators demonstrating a pH dependency, in some embodiments, comprise methyl violet, eosin yellow, malachite green, thymol blue, methyl yellow, bromophenol blue, congo red, methyl orange, methyl orange in xylene cyanole solution, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or combinations thereof.

A sintered porous matrix of a hydrophobic barrier composition, according to some embodiments, comprises at least one plastic in an amount ranging from about 95 weight percent to about 99.99 weight percent of the matrix. In other embodiments, a sintered porous matrix comprises at least one plastic in an amount ranging from about 98 weight percent to about 99.9 weight percent of the matrix.

In addition to the at least one plastic, a sintered porous matrix of a hydrophobic barrier composition comprises at least one color change indicator in an amount ranging from about 0.001 weight percent to about 2 weight percent of the matrix. In other embodiments, a sintered porous matrix comprises at least one color change indicator in an amount ranging from about 0.01 weight percent to about 1 weight percent of the matrix. In a further embodiment, a sintered porous matrix comprises at least one color change indicator in an amount ranging from about 0.05 weight percent to about 0.5 weight percent of the matrix.

A sintered porous matrix of a hydrophobic barrier composition comprising at least one plastic and at least one color change indicator, in some embodiments, has a porosity ranging from about 10% to about 90%. In another embodiment, a sintered porous matrix has a porosity ranging from about 20% to about 80% or from about 30% to about 70%. In a further embodiment, a sintered porous matrix has a porosity ranging from about 40% to about 60%.

A sintered porous matrix of a hydrophobic barrier composition comprising at least one plastic and at least one color change indicator, has an average pore size ranging from about 35 µm to about 200 µm. In other embodiments, a sintered porous matrix has an average pore size ranging from about 40 µm to about 150 µm, from about 60 µm to about 100 µm, or from about 70 µm to about 90 µm. In another embodiment, a porous sintered matrix has an average pore size less than about 1 µm. In one embodiment, a porous sintered matrix has an average pore size ranging from about 0.1 µm to about 1 µm.

In some embodiments, hydrophobic barrier compositions have a water intrusion pressure of greater than about 0.5 psi.

In another embodiment, the present invention provides a hydrophobic barrier composition comprising at least one plastic layer comprising a first plastic and at least one indicator layer comprising at least one color change indicator. In one embodiment, the indicator layer further comprises a second plastic. In some embodiments, the first plastic and the second plastic are the same. In other embodiments, the first plastic and the second plastic are different. Plastics suitable for use in the plastic layer and indicator layer, according to embodiments of the present invention comprise any of the plastics described herein. Moreover, color change indicators suitable for use in the indicator layer comprise any of the color change indicators described herein.

The plastic layer, in some embodiments, further comprises a color change indicator. In some embodiments, the color change indicator of the plastic layer is the same as the color change indicator of the indicator layer. In other embodiments, the color change indicator of the plastic layer is different than the color change indicator of the indicator layer.

In some embodiments, the at least one indicator layer is adjacent to the at least one plastic layer. In other embodiments, the at least one indicator layer is spaced apart from the at least one plastic layer. An indicator layer adjacent to or spaced apart from a plastic layer, in some embodiments, is operable to detect the intrusion of liquid into the hydrophobic barrier composition which could lead to contamination of downstream devices and apparatus.

In another embodiment, the indicator layer further comprises at least one surfactant. Surfactants, in some embodiments, comprise anionic surfactants, cationic surfactants, nonionic surfactants, amphoteric surfactants or mixtures thereof. In some embodiments, anionic surfactants comprise alkyl sulfates, alkylbenzenesulfonates, ether sulfates, a-olefin sulfonates, ester sulfonates, phosphate esters, acyl taurates, soaps, ether carboxylates, or mixtures thereof. Cationic surfactants, in some embodiments, comprise alkyl quaternary ammonium salts, bezylalkyldimethylammonium salts, amidoamine quaternaries, quaternary imidazolium compounds, ester quaternary compounds, or mixtures thereof. In some embodiments, nonionic surfactants comprise ethoxylated alcohols, ethoxylated alkylphenols, polyethylene glycol esters, fatty acid alkanolamides, ethoxylated alkanolamides, ethoxylated amines, esters of polyhydroxy compounds, ethoxylated esters, ethylene oxide/propylene oxide copolymers, amine oxides, or mixtures thereof. Amphoteric surfactants, in some embodiments, comprise alkylamino acids, alkylbetaines, alkylaminobetains, imidazoline-derived surfactants, sulfur containing amphoterics, lecithin, or mixtures thereof. In some embodiments, surfactants suitable for use in embodiments of the present invention comprise Geropon®, Rhodacal®, and Rhodafac® commercially available from Rhodia or Paris France, Pluronic® commercially available from BASF of Florham Park, N.J., and Zonyl® commercially available from DuPont of Wilmington, Del.

Indicator layers of hydrophobic barrier compositions comprising at least one surfactant, in some embodiments, demonstrate advantageous wicking properties allowing a rapid response to an aqueous and/or organic liquid contacting the indicator layer.

In some embodiments, plastic layers can demonstrate any construction described herein for sintered porous matrices of hydrophobic barrier compositions. Plastic layers, according to some embodiments, for example, can demonstrate pore sizes and/or porosities consistent with any the sintered porous matrices provided herein.

In some embodiments, indicator layers can demonstrate any construction described herein for sintered porous matrices of hydrophobic barrier compositions. Indicator layers, according to some embodiments, for example, can demonstrate pore sizes and/or porosities consistent with any the sintered porous matrices provided herein.

In some embodiments, a plastic layer is constructed independently from an indicator layer. In such embodiments, the plastic layer and the indicator layer can display similar pore sizes and/or porosities or different pore sizes and/or porosities.

Figure 3:
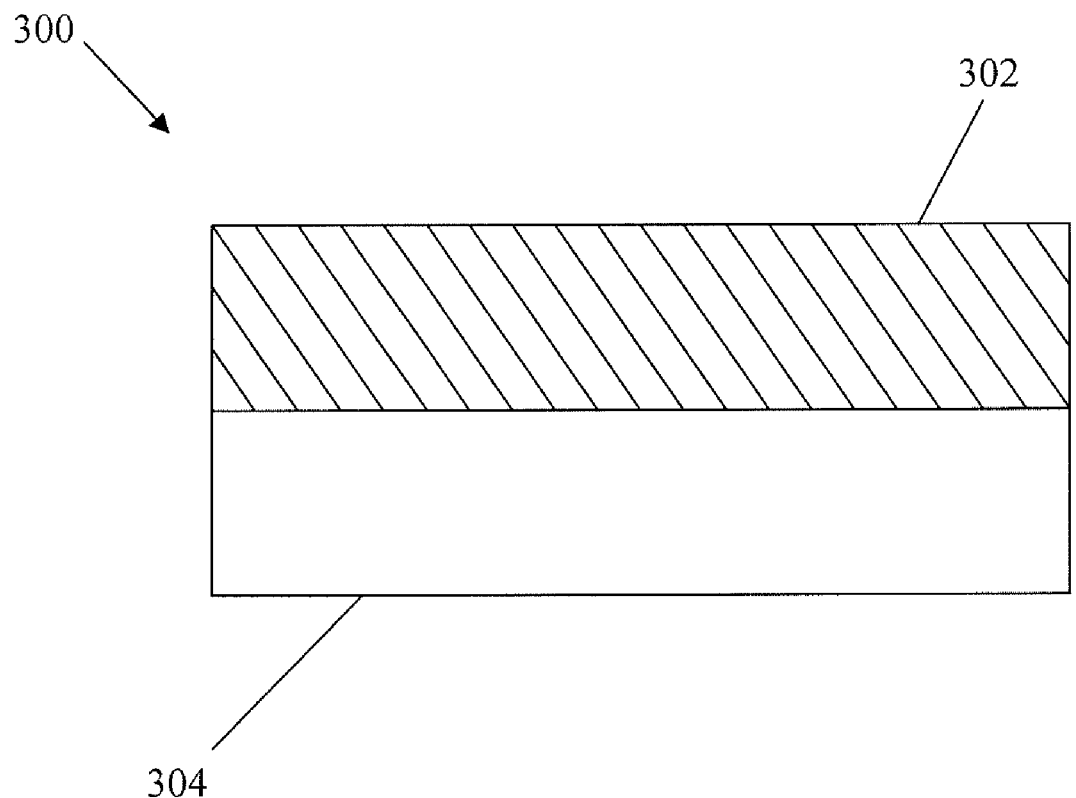
FIG. 3 illustrates a hydrophobic barrier composition according to an embodiment of the present invention.

FIG. 3 illustrates a hydrophobic barrier composition comprising a sintered porous matrix comprising at least one plastic layer and at least one indicator layer. The barrier composition (300) illustrated in FIG. 3 comprises a indicator layer (302) adjacent to the plastic layer (304). Liquid intrusion into the plastic layer can contact the indicator layer thereby alerting a user that the hydrophobic barrier composition has been compromised.

In a further embodiment, the present invention provides a hydrophobic barrier composition comprising a sintered porous matrix, the sintered porous matrix comprising a first surface and a second surface in facing opposition to the first surface, the first surface comprising at least one plastic and the second surface comprising at least one color change indicator. Plastics and color change indicators suitable for use in hydrophobic barrier compositions comprising an indicator surface in facing opposition to a plastic surface comprise any of the same described herein.

In some embodiments, the second surface of a hydrophobic barrier composition further comprises at least one surfactant.

In another embodiment, the first surface further comprises a color change indicator. In some embodiments, the color change indicator of the first surface is the same as the color change indicator of the second surface. In other embodiments, the color change indicator of the first surface is different from the color change indicator of the second surface.

Hydrophobic barrier compositions of the present invention, in some embodiments, exhibit a number of desirable properties including rapid response times, substantially no contamination of liquid samples, biocompatibility, and the ability to withstand high back pressures. In some embodiments, hydrophobic barrier compositions can tolerate back pressures of greater than about 1, 2, or 5 pounds per square inch (psi). Moreover, air flow rate through hydrophobic barrier compositions of the present invention, in some embodiments, is greater than about 16, 18, or 20 ml/minute. Hydrophobic barrier compositions of the present invention, in some embodiments, are also stable when exposed to ambient environmental conditions. Hydrophobic barrier compositions, in some embodiments, do not substantially respond to atmospheric moisture. In some embodiments, hydrophobic barrier compositions of the present invention produce no color change in response to atmospheric moisture. As a result, hydrophobic barrier compositions of the present invention can have a prolonged shelf life and require no special packaging or storage conditions.

Hydrophilic Compositions Comprising Color Change Indicators

In another embodiment, the present invention provides a hydrophilic composition comprising a sintered porous matrix, the sintered porous matrix comprising at least one plastic, at least one color change indicator, and at least one surfactant Turning now to components that can be included in hydrophilic compositions of the present invention, hydrophilic compositions of the present invention comprise at least one plastic. In some embodiments, hydrophilic compositions comprise a plurality of plastics.

Plastics suitable for use in sintered porous matrices of hydrophilic compositions, in some embodiments, comprise polyolefins, polyamides, polyesters, rigid polyurethanes, polyacrylonitriles, polycarbonates, polyvinylchloride, polymethylmethacrylate, polyvinylidene fluoride, polytetrafluoroethylene, polyethersulfones, polystyrenes, polyether imides, polyetheretherketones, polysulfones, or combinations or copolymers thereof.

In some embodiments, a polyolefin comprises polyethylene, polypropylene, and/or copolymers thereof. Polyethylene, in one embodiment, comprises HDPE. HDPE, as used herein, refers to polyethylene having a density ranging from about 0.92 g/cm$^3$ to about 0.97 g/cm$^3$. In some embodiments, HDPE has a degree of crystallinity (% from density) ranging from about 50 to about 90. In another embodiment, polyethylene comprises UHMWPE. UHMWPE, as used herein, refers to polyethylene having a molecular weight greater than 1,000,000.

In addition to at least one plastic, hydrophilic compositions of the present invention comprise at least one color change indicator. A color change indicator, according to embodiments of the present invention, is operable to at least partially change the color of the sintered porous matrix when contacted with an aqueous and/or organic liquid. In some embodiments, the color change indicator changes the sintered porous matrix from a first color to a second color when contacted with an aqueous and/or organic liquid. In other embodiments, the color change indicator changes the sintered porous matrix from colorless or white to colored. In a further embodiment, the color change indicator changes the sintered porous matrix from a first shade of a color to a different shade of the same color. The color change of the sintered porous matrix, according to embodiments of the present invention, depends on the identity of the color change indicator selected.

In some embodiments, a color change indicator comprises an inorganic or organic dye, including food grade dyes, azo compounds, or azo dyes. In some embodiments, a color change indicator does not comprise inorganic salts, including transition metal salts. Additionally, in some embodiments, a color change indicator does not comprise a conjugate or complex that changes color upon the binding of an analyte. In some embodiments, hydrophilic compositions of the present invention do not comprise proteins or other biological molecules.

Color change indicators comprising food grade dyes, according to embodiments of the present invention, are operable to be used with biological samples due to the non-toxic nature of the food dyes.

In some embodiments, a color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or combinations thereof.

Color change indicators, according to some embodiments, demonstrate a pH dependency on the color produced. As a result, color change indicators, in some embodiments, indicate not only liquid contact with the barrier composition but the relative pH of the contacting liquid as well. Color change indicators demonstrating a pH dependency, in some embodiments, comprise methyl violet, eosin yellow, malachite green, thymol blue, methyl yellow, bromophenol blue, congo red, methyl orange, methyl orange in xylene cyanole solution, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or combinations thereof.

Hydrophilic compositions of the present invention additionally comprise at least one surfactant. Surfactants, in some embodiments of hydrophilic compositions, comprise anionic surfactants, cationic surfactants, nonionic surfactants, amphoteric surfactants or mixtures thereof. In some embodiments, anionic surfactants comprise alkyl sulfates, alkylbenzenesulfonates, ether sulfates, α-olefin sulfonates, ester sulfonates, phosphate esters, acyl taurates, soaps, ether carboxylates, or mixtures thereof. Cationic surfactants, in some embodiments, comprise alkyl quaternary ammonium salts, bezylalkyldimethylammonium salts, amidoamine quaternaries, quaternary imidazolium compounds, ester quaternary compounds, or mixtures thereof. In some embodiments, nonionic surfactants comprise ethoxylated alcohols, ethoxylated alkylphenols, polyethylene glycol esters, fatty acid alkanolamides, ethoxylated alkanolamides, ethoxylated amines, esters of polyhydroxy compounds, ethoxylated esters, ethylene oxide/propylene oxide copolymers, amine oxides, or mixtures thereof. Amphoteric surfactants, in some embodiments, comprise alkylamino acids, alkylbetaines, alkylaminobetains, imidazoline-derived surfactants, sulfur containing amphoterics, lecithin, or mixtures thereof. In some embodiments, surfactants suitable for use in embodiments of the present invention comprise Geropon®, Rhodacal®, and Rhodafac® commercially available from Rhodia or Paris France, Pluronic® commercially available from BASF of Florham Park, N.J., and Zonyl® commercially available from DuPont of Wilmington, Del.

In some embodiments, a sintered porous matrix of a hydrophilic composition comprises at least one plastic in an amount of at least 90 weight percent of the matrix. A sintered porous matrix of a hydrophilic composition, according to some embodiments, comprises at least one plastic in an amount ranging from about 95 weight percent to about 99.99 weight percent of the matrix. In other embodiments, a sintered porous matrix comprises at least one plastic in an amount ranging from about 97 weight percent to about 99.9 weight percent of the matrix.

A sintered porous matrix of a hydrophilic composition of the present invention, in some embodiments, comprises at least one surfactant in an amount ranging from about 0.001 weight percent to about 3 weight percent of the matrix. In other embodiments, a sintered porous matrix comprises at least one surfactant in an amount ranging from about 0.01 weight percent to about 2 weight percent of the matrix. In a further embodiment, a sintered porous matrix comprises a at least one surfactant in an amount ranging from about 0.1 weight percent to about 1 weight percent of the matrix.

A sintered porous matrix of a hydrophilic composition comprising at least one plastic, at least one color change indicator, and at least one surfactant, in some embodiments, has a porosity ranging from about 10% to about 90%. In another embodiment, a sintered porous matrix has a porosity ranging from about 20% to about 80% or from about 30% to about 70%. In a further embodiment, a sintered porous matrix has a porosity ranging from about 40% to about 60%.

A sintered porous matrix of a hydrophilic composition comprising at least one plastic, at least one color change indicator, and at least one surfactant has an average pore size ranging from about 35 µm to about 200 µm. In other embodiments, a sintered porous matrix has an average pore size ranging from about 40 µm to about 150 µm, from about 60 µm to 100 µm, or from about 70 µm to about 90 µm. In another embodiment, a porous sintered matrix has an average pore size less than about 1 um. In one embodiment, a porous sintered matrix has an average pore size ranging from about 0.1 µm to about 1 µm.

Methods of Producing Self-Sealing Barrier Compositions

In another aspect, the present invention provides methods of producing self-sealing barrier compositions. In one embodiment, a method of producing a self-sealing barrier composition comprises providing particles of at least one plastic, providing particles of at least one absorbent material, providing particles of at least one color change indicator, and cosintering the particles of the at least one plastic, the at least one absorbent material, and the at least one color change indicator.

In some embodiments, particles of at least one plastic, particles of at least one absorbent material, and particles of at least one color change indicator are mixed in a desired ratio (weight percent) to product a substantially uniform mixture. The substantially uniform mixture of plastic, absorbent material, and color change indicator particles are disposed in a mold and sintered. The shape of the mold can be any desired shape.

Plastic particles, in some embodiments, have average sizes ranging from about 1 µm to about 1 mm. In another embodiment, plastic particles have average sizes ranging from about 10 µm to about 900 µm, from about 50 µm to about 500 µm, or from about 100 µm to about 400 µm. In a further embodiment, plastic particles have an average size ranging from about 200 µm to about 300 µm. In some embodiments, plastic particles have average sizes less than about 1 µm or greater than about 1 mm.

Particles of an absorbent material, according to some embodiments, have average sizes ranging from about 1 µm to about 500 µm or from about 10 µm to about 400 µm. In another embodiment, particles of an absorbent material have average sizes ranging from about 50 µm to about 300 µm. In a further embodiment, particles of an absorbent material have average sizes ranging from about 100 µm to about 200 µm. In some embodiments, particles of an absorbent material have average sizes less than about 1 µm or greater than about 500 µm.

Particles of a color change indicator, according to some embodiments, have average sizes ranging from about 1 µm to about 500 µm or from about 10 µm to about 400 µm. In another embodiment, particles of a color change indicator have average sizes ranging from about 50 µm to about 300 µm. In a further embodiment, particles of a color change indicator have average sizes ranging from about 100 µm to about 200 µm. In some embodiments, particles of a color change indicator have average sizes less than about 1 µm or greater than about 500 µm.

Particles of at least one plastic, at least one absorbent material, and at least one color change indicator, in some embodiments, are sintered at a temperature ranging from about 200° F. to about 700° F. In some embodiments, plastic, absorbent material, and color change indicator particles are sintered at a temperature of ranging from about 300° F. to about 500° F. The sintering temperature, according to embodiments of the present invention, is dependent upon and selected according to the identity of the plastic, absorbent material, and color change indicator particles.

Particles of at least one plastic, at least one absorbent material, and at least one color change indicator, in some embodiments, are sintered for a time period ranging from about 30 seconds to about 30 minutes. In other embodiments, particles of at least one plastic, at least one absorbent material, and at least one color change indicator are sintered for a time period ranging from about 30 seconds to about 15 minutes or from about 1 minute to about 10 minutes. In some embodiments, the sintering process comprises heating, soaking, and/or cooking cycles. Moreover, in some embodiments, sintering of particles of at least one plastic, at least one absorbent material, and at least one color change indicator is administered under ambient pressure (1 atm). In other embodiments, sintering particles of at least one plastic, at least one absorbent material, and at least one color change indicator is administered under pressures greater than ambient pressure.

In another embodiment, a method of producing a self-sealing barrier composition comprises disposing particles of at least one absorbent material in a first part of a mold, disposing particles of at least one color change indicator in a second part of the mold adjacent to the first part of the mold, and sintering the particles of the at least one absorbent material and the at least one color change indicator. In some embodiments, particles of a first plastic are mixed with particles of at the least one absorbent material prior to sintering. In some embodiments, particles of a second plastic are mixed with particles of the at least one color change indicator prior to sintering. In some embodiments, the first plastic and second plastic are the same. In other embodiments, the first plastic and second plastic are different.

In one embodiment, for example, particles of an absorbent material and particles of a first plastic are mixed in a desired ratio (weight percent) to produce a substantially uniform mixture. The mixture is disposed in the bottom half of a mold. Particles of a color change indicator and particles of a second plastic are mixed in a desired ratio (weight percent) to produce a substantially uniform mixture. The mixture of color change indicator and second plastic particles is disposed in the top half of the mold adjacent to the mixture of absorbent particles and first plastic particles. The absorbent particles, first plastic particles, color change indicator particles, and second plastic particles are subsequently sintered to produce a self-sealing barrier composition of the present invention. The barrier composition produced, in some embodiments, comprises a sintered porous matrix comprising a self-sealing layer and an indicator as described herein. The barrier composition produced, in other embodiments, comprises a sintered porous matrix comprising a self-sealing surface and an indicator surface as described herein.

Particles of an absorbent material, according to some embodiments, have average sizes ranging from about 1 μm to about 500 μm or from about 10 μm to about 400 μm. In another embodiment, particles of an absorbent material have average sizes ranging from about 50 μm to about 300 μm. In a further embodiment, particles of an absorbent material have average sizes ranging from about 100 μm to about 200 μm. In some embodiments, particles of an absorbent material have average sizes less than about 1 μm or greater than about 500 μm.

Particles of a color change indicator, according to some embodiments, have average sizes ranging from about 1 μm to about 500 μm or from about 10 μm to about 400 μm. In another embodiment, particles of a color change indicator have average sizes ranging from about 50 μm to about 300 μm. In a further embodiment, particles of a color change indicator have average sizes ranging from about 100 μm to about 200 μm. In some embodiments, particles of a color change indicator have average sizes less than about 1 μm or greater than about 500 μm.

First and second plastic particles, in some embodiments, individually have average sizes ranging from about 1 μm to about 1 mm. In another embodiment, plastic particles have average sizes ranging from about 10 μm to about 900 μm, from about 50 μm to about 500 μm, or from about 100 μm to about 400 μm. In a further embodiment, plastic particles have an average size ranging from about 200 μm to about 300 μm. In some embodiments, plastic particles have average sizes less than about 1 μm or greater than about 1 mm.

Absorbent material particles, color change indicator particles, first plastic particles, and second plastic particles, in some embodiments are sintered at a temperature ranging from about 200° F. to about 700° F. In some embodiments, absorbent particles, color change indicator particles, first plastic particles, and second plastic particles are sintered at a temperature of ranging from about 300° F. to about 500° F. The sintering temperature, according to embodiments of the present invention, is dependent upon and selected according to the identity of the plastic, absorbent material, and color change indicator particles.

Absorbent material particles, color change indicator particles, first plastic particles, and second plastic particles, in some embodiments, are sintered for a time period ranging from about 30 seconds to about 30 minutes. In other embodiments, absorbent material particles, color change indicator particles, first plastic particles, and second plastic particles are sintered for a time period ranging from about 30 seconds to about 15 minutes or from about 1 minute to about 10 minutes. In some embodiments, the sintering process comprises heating, soaking, and/or cooking cycles. Moreover, in some embodiments, sintering of absorbent material particles, color change indicator particles, first plastic particles, and second plastic particles is administered under ambient pressure (1 atm). In other embodiments, sintering is administered under pressures greater than ambient pressure.

In some embodiments, particles of at least one surfactant are mixed with particles of the at least one color change indicator prior to sintering. In other embodiments, particles of a second plastic are at least partially coated with at least one surfactant prior to sintering. In such embodiments, the surfactant can be applied to the second plastic particles as a liquid.

Particles of a surfactant, according to some embodiments, have average sizes ranging from about 0.1 μm to about 200 μm or from about 1 μm to about 150 μm. In another embodiment, particles of a surfactant have average sizes ranging from about 25 μm to about 100 μm. In a further embodiment, particles of a surfactant have average sizes ranging from about 30 μm to about 50 μm. In some embodiments, particles of a surfactant have average sizes greater than about 200 μm or less than about 0.1 μm. Compositions comprising surfactant particles are sintered in accordance with any of the embodiments provided herein.

In other embodiments, particles of a second color change indicator are mixed with particles of the at least one absorbent material prior to sintering. In some embodiments, particles of the at least one color change indicator and particles of the second color change indicator are the same. In another embodiment, particles of the at least one color change indicator and particles of the second color change indicator are different.

Methods of Producing Hydrophobic Barrier Compositions

In another aspect, the present invention provides methods of producing hydrophobic barrier compositions. In one embodiment, a method of producing a hydrophobic barrier composition comprises providing particles of at least one plastic, providing particles of at least one color change indicator, and cosintering the particles of the at least one plastic and the at least one color change indicator.

In some embodiments, particles of at least one plastic and particles of at least one color change indicator are mixed in a desired ratio (weight percent) to produce a substantially uniform mixture. The substantially uniform mixture of plastic and color change indicator particles is disposed in a mold and sintered. The shape of the mold can be any desired shape.

Plastic particles, in some embodiments, have average sizes ranging from about 1 μm to about 1 mm. In another embodiment, plastic particles have average sizes ranging from about 10 μm to about 900 μm, from about 50 μm to about 500 μm, or from about 100 μm to about 400 μm. In a further embodiment, plastic particles have an average size ranging from about 200 µm to about 300 µm. In some embodiments, plastic particles have average sizes less than about 1 µm or greater than about 1 mm.

Particles of a color change indicator, according to some embodiments, have average sizes ranging from about 1 µm to about 500 µm or from about 10 µm to about 400 µm. In another embodiment, particles of a color change indicator have average sizes ranging from about 50 µm to about 300 µm. In a further embodiment, particles of a color change indicator have average sizes ranging from about 100 µm to about 200 µm. In some embodiments, particles of a color change indicator have average sizes less than about 1 µm or greater than about 500 µm.

Particles of at least one plastic and at least one color change indicator, in some embodiments, are sintered at a temperature ranging from about 200° F. to about 700° F. In some embodiments, plastic and color change indicator particles are sintered at a temperature of ranging from about 300° F. to about 500° F. The sintering temperature, according to embodiments of the present invention, is dependent upon and selected according to the identity of the plastic and color change indicator particles.

Particles of at least one plastic and at least one color change indicator, in some embodiments, are sintered for a time period ranging from about 30 seconds to about 30 minutes. In other embodiments, particles of at least one plastic and at least one color change indicator are sintered for a time period ranging from about 30 seconds to about 15 minutes or from about 1 minute to about 10 minutes. In some embodiments, the sintering process comprises heating, soaking, and/or cooking cycles. Moreover, in some embodiments, sintering of particles of at least one plastic and at least one color change indicator is administered under ambient pressure (1 atm). In other embodiments, sintering particles of at least one plastic and at least one color change indicator is administered under pressures greater than ambient pressure.

In a further embodiment, a method for producing a hydrophobic barrier material comprises disposing particles of a first plastic in first part of a mold, disposing particles of at least one color change indicator in a second part of the mold adjacent to the first part of the mold, and sintering the particles of the first plastic and the at least one color change indicator. In some embodiments, particles of a second plastic are mixed with particles of the at least one color change indicator prior to sintering. In one embodiment, the first and second plastics are the same. In another embodiment, the first and second plastics are different.

In one embodiment, for example, particles of a first plastic are disposed in the bottom half of a mold. Particles of a color change indicator and particles of a second plastic are mixed in a desired ratio (weight percent) to produce a substantially uniform mixture. The mixture of color change indicator and second plastic particles is disposed in the top half of the mold adjacent to the first plastic particles. The first plastic particles, color change indicator particles, and second plastic particles are subsequently sintered to produce a hydrophobic barrier composition of the present invention. The hydrophobic barrier composition produced, in some embodiments, comprises a sintered porous matrix comprising a plastic layer and an indicator layer comprising a color change indicator as described herein. The hydrophobic barrier composition produced, in other embodiments, comprises a sintered porous matrix comprising a first surface and a second surface, the first surface comprising at least one plastic and the second surface comprising at least one color change indicator as described herein.

Particles of a color change indicator, according to some embodiments, have average sizes ranging from about 1 µm to about 500 µm or from about 10 µm to about 400 µm. In another embodiment, particles of a color change indicator have average sizes ranging from about 50 µm to about 300 µm. In a further embodiment, particles of a color change indicator have average sizes ranging from about 100 µm to about 200 µm. In some embodiments, particles of a color change indicator have average sizes less than about 1 µm or greater than about 500 µm.

First and second plastic particles, in some embodiments, individually have average sizes ranging from about 1 µm to about 1 mm. In another embodiment, plastic particles have average sizes ranging from about 10 µm to about 900 µm, from about 50 µm to about 500 µm, or from about 100 µm to about 400 µm. In a further embodiment, plastic particles have an average size ranging from about 200 µm to about 300 µm. In some embodiments, plastic particles have average sizes less than about 1 µm or greater than about 1 mm.

Color change indicator particles, first plastic particles, and second plastic particles, in some embodiments are sintered at a temperature ranging from about 200° F. to about 700° F. In some embodiments, color change indicator particles, first plastic particles, and second plastic particles are sintered at a temperature of ranging from about 300° F. to about 500° F. The sintering temperature, according to embodiments of the present invention, is dependent upon and selected according to the identity of the plastic, absorbent material, and color change indicator particles.

Color change indicator particles, first plastic particles, and second plastic particles, in some embodiments, are sintered for a time period ranging from about 30 seconds to about 30 minutes. In other embodiments, color change indicator particles, first plastic particles, and second plastic particles are sintered for a time period ranging from about 30 seconds to about 15 minutes or from about 1 minutes to about 10 minute. In some embodiments, the sintering process comprises heating, soaking, and/or cooking cycles. Moreover, in some embodiments, sintering of color change indicator particles, first plastic particles, and second plastic particles is administered under ambient pressure (1 atm). In other embodiments, sintering is administered under pressures greater than ambient pressure.

In some embodiments, particles of at least one surfactant are mixed with particles of the at least one color change indicator prior to sintering. In other embodiments, particles of a second plastic are at least partially coated with at least one surfactant prior to sintering. In such embodiments, the surfactant can be applied to the second plastic particles as a liquid.

Particles of a surfactant, according to some embodiments, have average sizes ranging from about 0.1 µm to about 200 µm or from about 1 µm to about 150 µm. In another embodiment, particles of a surfactant have an average sizes ranging from about 25 µm to about 100 µm. In a further embodiment, particles of a surfactant have average sizes ranging from about 30 µm to about 50 µm. In some embodiments, particles of a surfactant have average sizes greater than about 200 µm or less than about 0.1 µm. Compositions comprising surfactant particles are sintered in accordance with any of the embodiments provided herein.

Methods of Producing Hydrophilic Compositions

In another aspect, the present invention provides methods of producing hydrophilic compositions. In one embodiment, a method of producing a hydrophilic composition comprises providing particles of at least one plastic, providing particles of at least one color change indicator, providing particles of at least one surfactant, and cosintering the particles of the at least one plastic, the at least one color change indicator, and at least one surfactant.

In some embodiments, particles of at least one plastic, particles of at least one color change indicator, and particles of at least one surfactant are mixed in a desired ratio (weight percent) to produce a substantially uniform mixture. The substantially uniform mixture of plastic, color change indicator, and surfactant particles is disposed in a mold and sintered. The shape of the mold can be any desired shape.

Plastic particles, in some embodiments, have average sizes ranging from about 1 µm to about 1 mm. In another embodiment, plastic particles have average sizes ranging from about 10 µm to about 900 µm, from about 50 µm to about 500 µm, or from about 100 µm to about 400 µm. In a further embodiment, plastic particles have an average size ranging from about 200 µm to about 300 µm. In some embodiments, plastic particles have average sizes less than about 1 µm or greater than about 1 mm.

Particles of a color change indicator, according to some embodiments, have average sizes ranging from about 1 µm to about 500 µm or from about 10 µm to about 400 µm. In another embodiment, particles of a color change indicator have average sizes ranging from about 50 µm to about 300 µm. In a further embodiment, particles of a color change indicator have average sizes ranging from about 100 µm to about 200 µm. In some embodiments, particles of a color change indicator have average sizes less than about 1 µm or greater than about 500 µm.

Particles of a surfactant, according to some embodiments, have average sizes ranging from about 0.1 µm to about 200 µm or from about 1 µm to about 150 µm. In another embodiment, particles of a surfactant have average sizes ranging from about 25 µm to about 100 µm. In a further embodiment, particles of a surfactant have average sizes ranging from about 30 µm to about 50 µm. In some embodiments, particles of a surfactant have average sizes greater than about 200 µm or less than about 0.1 µm Particles of at least one plastic, at least one color change indicator, and at least one surfactant, in some embodiments, are sintered at a temperature ranging from about 200° F. to about 700° F. In some embodiments, plastic, color change indicator, and surfactant particles are sintered at a temperature of ranging from about 300° F. to about 500° F. The sintering temperature, according to embodiments of the present invention, is dependent upon and selected according to the identity of the plastic, color change indicator, and surfactant particles.

Particles of at least one plastic, at least one color change indicator, and at least one surfactant, in some embodiments, are sintered for a time period ranging from about 30 seconds to about 30 minutes. In other embodiments, particles of at least one plastic, at least one color change indicator, and at least one surfactant are sintered for a time period ranging from about 30 seconds to about 15 minutes or from about 1 minute to about 10 minutes. In some embodiments, the sintering process comprises heating, soaking, and/or cooking cycles. Moreover, in some embodiments, sintering of particles of at least one plastic and at least one color change indicator is administered under ambient pressure (1 atm). In other embodiments, sintering particles of at least one plastic and at least one color change indicator is administered under pressures greater than ambient pressure.

In another embodiment, a method of producing a hydrophilic composition comprises providing particles of at least one plastic, at least partially coating the particles of the at least one plastic with at least one surfactant, providing particles of at least one color change indicator, and sintering the particles of the at least one plastic and particles of the at least one color change indicator. Plastic particles coated with at least one surfactant and particles of at least one color change indicator, in some embodiments, are sintered in accordance with any of the methods provided herein. In some embodiments, particles of color change indicators are at least partially coated with at least one surfactant prior to sintering.

Apparatus Comprising Barrier Compositions

In another aspect, the present invention provides apparatus comprising barrier compositions of the present invention. In one embodiment, an apparatus comprises a pipette tip, the pipette tip comprises a hollow tube comprising first and second open ends, a center member disposed between the first and second ends, the center member comprising a barrier composition according to any of the embodiments provided herein. In some embodiments, the pipette tip has a volume of about 10 µl or about 20 µl. In other embodiments, the pipette tip has a sample volume of about 50 µl or about 100 µl. In another embodiment, the pipette tip has a sample volume of about 200 µl, about 250 µl, about 500 µl, or about 1 ml. In a further embodiment, the pipette tip has a sample volume less than about 10 µl or greater than about 1 ml or about 5 ml. In some embodiments, the pipette tip has a sample volume of about 1 µl or about 5 µl.

Figure 4:
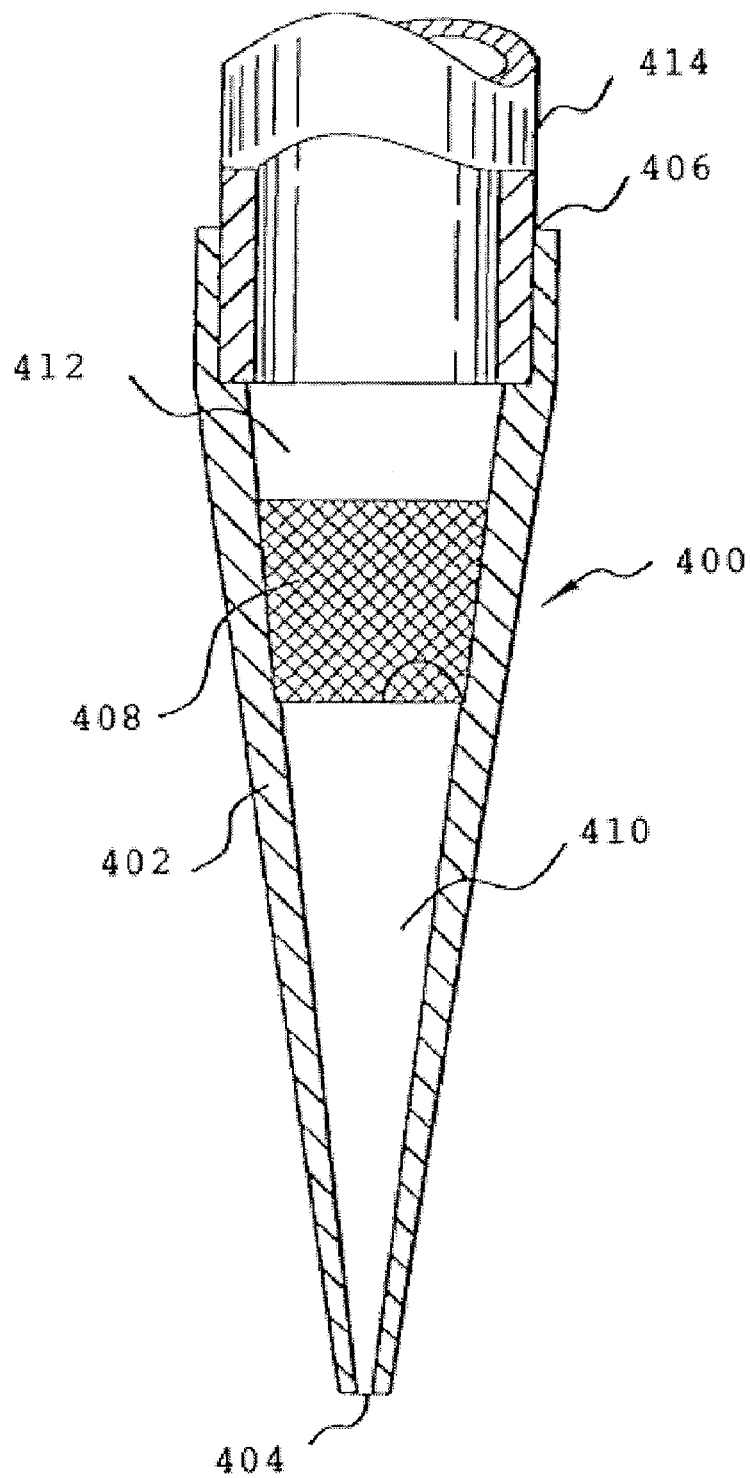
FIG. 4 illustrates a pipette tip comprising a barrier composition according to an embodiment of the present invention.

FIG. 4 illustrates a pipette tip comprising a barrier composition of the present invention. The pipette tip (400) comprises a tapering, hollow tubular member (402), the hollow tubular member, in some embodiments, comprising a non-reactive material such as glass, polyethylene, or other polymeric material. The hollow tubular member (402) is open at a first end (404) and a second end (406), the first (404) and second (406) ends in facing opposition. A barrier composition (408) of the present invention is disposed in the hollow tubular member (402) to define a liquid sample chamber (410) between barrier composition (408) and the first end (404). The barrier composition is additionally spaced apart from the second end (406) to define a chamber (412) between the barrier composition (408) and the second end (406). The second end (406) is releasably secured to the a suitable suction device (414) in any manner known to one of skill in the art.

In another embodiment, barrier compositions of the present invention find application as flow control devices in various apparatus such as aspirators. In one embodiment, an aspirator comprises a receptacle, a lid, and a barrier composition according to any of the embodiments provided herein. The barrier composition is disposed in the receptacle. Moreover, the lid further comprises an inlet and an outlet wherein outlet is operable to be connected to a suction or vacuum line. In some embodiments, a self-sealing barrier composition covers the outlet such that when sufficient liquid has been collected in the receptacle, contact of the liquid to the barrier composition results in self-sealing of the barrier composition. The sealing of the barrier composition prevents or inhibits further aspiration.

In another embodiment, barrier compositions of the present invention find application in needle apparatus such as an indwelling needle as described in U.S. patent application Ser. No. 11/065,579; a flashback blood collection needle as described in U.S. patent application Ser. No. 11/141,588; a blood collection set as described in U.S. patent application Ser. No. 11/141,446; and a luer cap associated with an IV set. In these applications, barrier compositions of the present invention are incorporated as vents, allowing the passage of air and other gases while blocking the passage of liquids such as blood.

In a further embodiment, barrier compositions of the present invention find application in analytical devices to indicate that sufficient liquid sample has been collected. In some embodiments, an analytical device comprises a liquid sample collection chamber comprising a sample inlet and a barrier composition disposed within the sample collection chamber. The barrier composition, in some embodiments, can be disposed at various levels in the collection chamber depending on the desired volume of sample to be collected. When sufficient sample has been collected, liquid contacts the barrier composition rendering a color change in the medium. The color change in the barrier composition can indicate to a user of the analytical device that sufficient sample has been collected. In some embodiments, the liquid sample chamber further comprises an outlet.

Embodiments of the present invention a further illustrated in the following non-limiting examples.

Example 1

Self-Sealing Barrier Composition Comprising Color Change Indicator

Powdered HDPE having an average particle size of about 150 μm was mixed with carboxymethylcellulose (CMC), and food dye erioglaucine producing a substantially uniform mixture of 84.95 weight percent polyethylene, 15 weight percent CMC, and 0.05 weight percent food dye erioglaucine. The resulting mixture was disposed in a metal mold and heated to 350° F. for about three minutes and subsequently cooled to room temperature in about five minutes. The resulting self-sealing barrier composition had an average pore size of about 40 μm and a white color. When contacted with an aqueous liquid, the barrier composition turned a blue color.

Example 2

Hydrophobic Barrier Composition Comprising Color Change Indicator

Powdered HDPE having an average particle size of about 30 μm was mixed with food dye erioglaucine producing a substantially uniform mixture of 99.95 weight percent polyethylene and 0.05 weight percent food dye erioglaucine. The resulting mixture was disposed in a metal mold and heated to 350° F. for about three minutes and subsequently cooled to room temperature in about five minutes. The resulting self-sealing barrier composition had an average pore size of about 10 μm and a white color. When contacted with an aqueous liquid, the barrier composition turned a blue color and demonstrated a water contact angle greater than 90°.

Example 3

Layered Self-Sealing Barrier Composition Comprising Color Change Indicator

Powdered HDPE having an average particle size of about 30 μm is mixed with food dye erioglaucine producing a substantially uniform mixture of 99.95 weight percent polyethylene and 0.05 weight percent food dye erioglaucine. The polyethylene/food dye mixture is disposed in the bottom part of a metal mold.

Powdered HDPE having an average particle size of about 150 μm is combined with carboxymethylcellulose (CMC), and food dye erioglaucine producing a substantially uniform mixture of 84.95 weight percent polyethylene, 15 weight percent CMC, and 0.05 weight percent food dye erioglaucine. The resulting mixture is disposed in the top half of the metal mold adjacent to the bottom half. The mold is heated to 350° F. for about three minutes and is subsequently cooled to room temperature in about five minutes. The resulting barrier composition has a first layer demonstrating hydrophobic color changing properties and a second layer demonstrating self-sealing color change properties.

Example 4

Layered Self-Sealing Barrier Composition Comprising Color Change Indicator

Powdered HDPE having an average particle size of about 150 μm is mixed with sodium dodecyl sulfate (Sigma-Aldrich) and food dye erioglaucine producing a substantially uniform mixture of 99.5 weight percent polyethylene, 0.45 weight percent sodium dodecyl sulfate, and 0.05 weight percent erioglaucine. The polyethylene/surfactant/food dye mixture is disposed in the bottom half of a metal mold.

Powdered HDPE having an average particle size of about 150 μm is mixed with carboxymethylcellulose (CMC), and food dye erioglaucine producing a substantially uniform mixture of 84.95 weight percent polyethylene, 15 weight percent CMC, and 0.05 weight percent food dye erioglaucine. The resulting mixture is disposed in the top half of the metal mold adjacent to the bottom half. The mold is heated to 350° F. for about three minutes and subsequently cooled to room temperature in about five minutes. The resulting barrier composition has a first layer demonstrating hydrophilic color changing properties and a second layer demonstrating self-sealing color change properties.

Example 5

Hydrophilic Composition

Powdered HDPE having an average particle size of about 150 μm was mixed with sodium dodecyl sulfate (Sigma-Aldrich) and food dye erioglaucine to produce a substantially uniform mixture of 99.5 weight percent polyethylene, 0.45 weight percent sodium dodecyl sulfate, and 0.05 weight percent erioglaucine. The resulting mixture was disposed in a metal mold and heated to 350° F. for about three minutes and subsequently cooled to room temperature in about five minutes. The resulting hydrophilic composition had an average pore size of about 40 μm and a white color. Aqueous solution wicks into the hydrophilic composition upon contact. Moreover, the hydrophilic composition turned blue when contacted with an aqueous solution.

Example 6

Pipette Tip Comprising a Self-Sealing Barrier Composition

The self-sealing barrier composition of Example 1 was disposed in a pipette tip by inserting the self-sealing barrier composition through the end of the pipette tip operable to receive the pipettor. Sufficient pressure was applied to the self-sealing barrier composition during insertion to ensure that the barrier composition formed a seal with the interior surfaces of the pipette tip. After insertion of the barrier medium into the pipette tip, the pipette tip was attached to a pipettor. The pipette tip was placed in an aqueous solution, and the aqueous solution was drawn into the sample collection chamber of the pipette tip. As the aqueous solution was being drawn into the sample collection chamber, the pipette tip was removed from the aqueous solution resulting in aspiration, thereby bringing the aqueous solution into contact with the self-sealing barrier composition. Upon contact with the aqueous solution, the CMC of the barrier composition expanded and sealed the barrier composition precluding any aqueous solution from reaching the pipettor. The barrier medium additionally changed color indicating that the barrier medium had come into contact with the aqueous solution. Moreover, none of the aqueous solution circumvented barrier medium.

All patents, patent applications, publications, and abstracts cited above are incorporated herein by reference in their entirety. Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention.

That which is claimed is:

1. A self-sealing barrier composition comprising:
a sintered porous matrix, the sintered porous matrix comprising at least one plastic, at least one absorbent material, and particles of at least one color change indicator, wherein the particles of the at least one color change indicator in the sintered porous matrix dissolve upon contact with liquid and at least partially change the color of the sintered porous matrix, and the sintered porous matrix is self-sealing upon contact with the liquid.

2. The self-sealing barrier composition of claim 1, wherein the at least one color change indicator comprises an organic dye, food grade dye, or mixtures thereof.

3. The self-sealing barrier composition of claim 2, wherein the color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or mixtures thereof.

4. The self-sealing barrier composition of claim 1, wherein the color change indicator is responsive to pH.

5. The self-sealing barrier composition of claim 4, wherein the color change indicator comprises methyl violet, eosin yellow, malachite green, thymol blue, methyl yellow, bromophenol blue, congo red, methyl orange, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or mixtures thereof.

6. The self-sealing barrier composition of claim 1, wherein the at least one absorbent material comprises carboxymethylcellulose, cellulose gums, hydrolyzed acrylonitrile graft copolymer, neutralized starch-acrylic acid graft copolymer, acrylamide copolymer, modified crosslinked polyvinyl alcohol, neutralized self-crosslinking polyacrylic acid, crosslinked polyacrylate salts, neutralized crosslinked isobutylene-maleic anhydride copolymers, or salts or mixtures thereof.

7. The self-sealing barrier composition of claim 1, wherein the at least one plastic comprises a polyolefin, polyamide, polyester, polyurethane, polyacrylonitrile, polycarbonate, polyvinylchloride, polymethylmethacrylate, polyvinylidene fluoride, polytetrafluoroethylene, polyethersulfone, polystyrene, polyether imide, polyetheretherketone, polysulfone, or combinations or copolymers thereof.

8. The self-sealing barrier composition of claim 7, wherein the polyolefin comprises polyethylene, polypropylene, polybutylene, or combinations or copolymers thereof.

9. The self-sealing barrier composition of claim 1, wherein the at least one color change indicator is present in an amount ranging from about 0.001 weight percent to about 2 weight percent of the sintered porous matrix.

10. The self-sealing barrier composition of claim 1, wherein the at least one color change indicator is present in an amount ranging from about 0.05 weight percent to about 0.5 weight percent of the sintered porous matrix.

11. The self-sealing barrier composition of claim 1, wherein the at least one plastic is present in an amount ranging from about 40 weight percent to about 95 weight percent of the sintered porous matrix.

12. The self-sealing barrier composition of claim 1, wherein the sintered porous matrix has an average pore size ranging from about 1 μm an to about 200 μm.

13. The self-sealing barrier composition of claim 1, wherein the sintered porous matrix has a porosity of up to about 90%.

14. The self-sealing barrier composition of claim 1, wherein the self-sealing barrier composition is not responsive to ambient atmospheric moisture.

15. An apparatus comprising:
a pipette tip and the self-sealing barrier composition of claim 1, wherein the self-sealing barrier composition of claim 1 is at least partially disposed in the pipette tip.

16. An apparatus comprising:
an aspirator, the aspirator comprising a receptacle, an inlet to the receptacle, and an outlet to the receptacle, wherein the self-sealing barrier composition of claim 1 at least partially covers the outlet of the receptacle.

17. An analytical device comprising:
a liquid sample collection chamber comprising a sample inlet and the self-sealing barrier composition of claim 1 disposed within the sample collection chamber.

18. The self-sealing barrier composition of claim 1, wherein the at least one color change indicator does not comprise inorganic salts.

19. The self-sealing barrier composition of claim 1, wherein the at least one color change indicator does not comprise a conjugate or complex that changes color upon the binding of an analyte.

20. The self-sealing barrier composition of claim 1, wherein the at least one color change indicator does not comprise proteins or other biological molecules.

21. A self-sealing barrier composition comprising:
a sintered porous matrix, the sintered porous matrix comprising at least one self-sealing layer and at least one indicator layer, wherein the self-sealing layer comprises at least one absorbent material and the indicator layer comprises particles of at least one color change indicator, wherein the particles of the at least one color change indicator in the indicator layer dissolve upon contact with liquid and at least partially change the color of the indicator layer, and the self-sealing layer is self-sealing upon contact with the liquid.

22. The self-sealing barrier composition of claim 21, wherein the at least one color change indicator comprises an organic dye, food grade dye, or mixtures thereof.

23. The self-sealing barrier composition of claim 22, wherein the color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or mixtures thereof.

24. The self-sealing barrier composition of claim 21, wherein the self-sealing layer is adjacent to the indicator layer.

25. The self-sealing barrier composition of claim 21, wherein the self-sealing layer is spaced apart from the indicator layer.

26. The self-sealing barrier composition of claim 21, wherein the self-sealing layer further comprises a second color change indicator.

27. The self-sealing barrier composition of claim 26, wherein the second color change indicator is different than the color change indicator of the indicator layer.

28. The self-sealing barrier composition of claim 21, wherein the self-sealing layer further comprises at least one plastic.

29. A self-sealing barrier composition comprising:
a sintered porous matrix, the sintered porous matrix comprising a self-sealing surface and an indicator surface in facing opposition to the self-sealing surface wherein the self-sealing surface comprises at least one absorbent material and the indicator surface comprises particles of at least one color change indicator, wherein the particles of the at least one color change indicator in the indicator surface dissolve upon contact with liquid and at least partially change the color of the indicator surface, and the self-sealing surface is self-sealing upon contact with the liquid.

30. A hydrophobic barrier composition comprising:
a sintered porous matrix, the sintered porous matrix comprising at least one plastic and particles of at least one color change indicator, wherein the hydrophobic barrier composition is substantially free of any absorbent material, wherein the particles of the at least one color change indicator in the sintered porous matrix dissolve upon contact with liquid and at least partially change the color of the sintered porous matrix, and the sintered porous matrix inhibits the liquid from passing through the hydrophobic barrier composition upon contact with the liquid.

31. The hydrophobic barrier composition of claim 30, wherein the at least one color change indicator comprises an organic dye, food grade dye, or mixtures thereof.

32. The hydrophobic barrier composition of claim 31, wherein the color change indicator comprises FD&C Blue No. 1, FD&C Blue No. 2, FD&C Green No. 3, FD&C Red No. 40, FD&C Red No. 3, FD&C Yellow No. 5, FD&C Yellow No. 6, Solvent Red 24, Solvent Red 26, Solvent Red 164, Solvent Yellow 124, Solvent Blue 35, or mixtures thereof.

33. The hydrophobic barrier composition of claim 30, wherein the color change indicator is responsive to pH.

34. The hydrophobic barrier composition of claim 33, wherein the color change indicator comprises methyl violet, eosin yellow, malachite green, thymol blue, methyl yellow, bromophenol blue, congo red, methyl orange, bromocresol green, methyl red, litmus, bromocresol purple, bromophenol red, bromothymol blue, phenol red, neutral red, naphtholphthalein, cresol red, phenolphthalein, thymolphthalein, alkali blue, Alizarin Yellow R, indigo carmine, epsilon blue, or mixtures thereof.

35. The hydrophobic barrier composition of claim 30, wherein the at least one color change indicator is present in an amount ranging from about 0.001 weight percent to about 2 weight percent of the sintered porous matrix.

36. The hydrophobic barrier composition of claim 30, wherein the at least one color change indicator is present in an amount ranging from about 0.05 weight percent to about 0.5 weight percent of the sintered porous matrix.

37. The hydrophobic barrier composition of claim 30, wherein the sintered porous matrix has an average pore size ranging from about 1 µm to about 200 µm.

38. A hydrophilic composition comprising:
a sintered porous matrix, the sintered porous matrix comprising at least one plastic, particles of at least one color change indicator, and at least one surfactant, wherein the particles of the at least one color change indicator dissolve upon contact with liquid and at least partially change the color of the sintered porous matrix.

39. The hydrophilic composition of claim 38, wherein the at least one surfactant comprises anionic surfactants, cationic surfactants, nonionic surfactants, amphoteric surfactants, or mixtures thereof.

40. The hydrophilic composition of claim 38, wherein the at least one surfactant is present in an amount ranging from about 0.001 weight percent to about 3 weight percent of the sintered porous matrix.

41. A method of making a self-sealing barrier composition comprising:
providing particles of at least one plastic;
providing particles of at least one absorbent material;
providing particles of at least one color change indicator; and
cosintering the particles of the at least one plastic, the particles of the at least one absorbent material, and the particles of the at least one color change indicator to form the self-sealing barrier composition, wherein the particles of the at least one color change indicator dissolve upon contact with liquid and the self-sealing barrier composition at least partially changes color and is self-sealing upon contact with the liquid.

42. The method of claim 41, further comprising mixing the particles of the at least one plastic, the particles of the at least one absorbent material, and the particles of the at least one color change indicator to form a substantially uniform mixture.

43. The method of claim 41, wherein the particles of the at least one plastic have an average diameter ranging from about 1 µm to about 500 µm.

44. A hydrophobic barrier composition comprising:
a sintered porous matrix, the sintered porous matrix comprising at least one plastic and at particles of least one color change indicator, wherein the particles of the at least one color change indicator in the sintered porous matrix dissolve upon contact with liquid and at least partially change the color of the sintered porous matrix, and the sintered porous matrix inhibits the liquid from passing through the hydrophobic barrier composition upon contact with the liquid.

* * * * *